(12) United States Patent
Schmeitz et al.

(10) Patent No.: US 12,178,653 B2
(45) Date of Patent: Dec. 31, 2024

(54) ULTRASOUND ANALYSIS METHOD AND DEVICE

(71) Applicant: KONINKLIJKE PHILIPS N.V., Eindhoven (NL)

(72) Inventors: Harold Agnes Wilhelmus Schmeitz, Eindhoven (NL); Frederik Jan De Bruijn, Eindhoven (NL); Gerhardus Wilhelmus Lucassen, Eindhoven (NL); Vincent Maurice André Auvray, Meudon (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 123 days.

(21) Appl. No.: 17/430,600

(22) PCT Filed: Feb. 14, 2020

(86) PCT No.: PCT/EP2020/053841
§ 371 (c)(1),
(2) Date: Aug. 12, 2021

(87) PCT Pub. No.: WO2020/165389
PCT Pub. Date: Aug. 20, 2020

(65) Prior Publication Data
US 2022/0142606 A1     May 12, 2022

(30) Foreign Application Priority Data
Feb. 14, 2019   (EP) ...................................... 19290011

(51) Int. Cl.
*A61B 8/08* (2006.01)
*A61B 8/12* (2006.01)
(Continued)

(52) U.S. Cl.
CPC .......... *A61B 8/5207* (2013.01); *A61B 8/0841* (2013.01); *A61B 8/0891* (2013.01);
(Continued)

(58) Field of Classification Search
CPC ....... A61B 8/0841; A61B 8/0891; A61B 8/12; A61B 8/4494
See application file for complete search history.

(56) References Cited

U.S. PATENT DOCUMENTS 8,831,321 B1 * 9/2014 Elbasiony ............ A61B 5/1076
382/131
9,519,840 B2    12/2016 Joo
(Continued)

FOREIGN PATENT DOCUMENTS

WO      2011015952 A1    2/2011

OTHER PUBLICATIONS

International Search Report and Written Opinion of PCT/EP2020/053841, dated May 8, 2020.
(Continued)

*Primary Examiner* — Amal Aly Farag

(57) ABSTRACT

The invention provides an ultrasound data processing method (30) for detecting presence of an intravascular object in a vessel lumen based on analysis of acquired intravascular ultrasound data of the lumen. The method comprises receiving (32) data comprising multiple frames, and each frame containing data for a plurality of radial lines, corresponding to different circumferential positions around the IVUS device body, and reducing (34) the data to a single representative value for each radial line in each frame. These representative values are subsequently processed to derive (36) values for at least each frame representative of a probability of presence of an object within the given frame. Based on the probability values, a region within the data
(Continued)

occupied by an intravascular object, for instance a consecutive set of frames occupied by an object, is determined (38).

14 Claims, 7 Drawing Sheets

(51) Int. Cl.
*G06V 10/44* (2022.01)
*G06V 10/82* (2022.01)
*A61B 8/00* (2006.01)

(52) U.S. Cl.
CPC .............. *A61B 8/12* (2013.01); *A61B 8/5223* (2013.01); *G06V 10/446* (2022.01); *G06V 10/82* (2022.01); *A61B 8/085* (2013.01); *A61B 8/4494* (2013.01); *G06V 2201/034* (2022.01)

(56) References Cited

U.S. PATENT DOCUMENTS

| | | | | |
|---|---|---|---|---|
| 10,646,198 | B2* | 5/2020 | Peterson | A61B 8/12 |
| 2008/0004530 | A1* | 1/2008 | Feldman | G06T 7/33 |
| | | | | 600/467 |
| 2008/0075375 | A1* | 3/2008 | Unal | G06T 7/174 |
| | | | | 382/243 |
| 2011/0071404 | A1 | 3/2011 | Schmitt | |
| 2012/0130243 | A1 | 5/2012 | Balocco | |
| 2014/0249423 | A1 | 9/2014 | Cai | |
| 2014/0268167 | A1 | 9/2014 | Friedman | |
| 2015/0073279 | A1 | 3/2015 | Cai | |
| 2016/0345819 | A1* | 12/2016 | Jayasundera | G06T 7/12 |
| 2017/0024910 | A1 | 1/2017 | Griffin | |
| 2017/0148161 | A1* | 5/2017 | Griffin | A61B 5/0066 |

OTHER PUBLICATIONS

Carlier, Stephane G. et al "Guidance of Intracoronary Radiation Therapy based on Dose-Volume Histograms Derived from Quantitative Intravascular Ultrasound" IEEE Transactions on Medical Imaging, vol. 17, No. 5, Oct. 1998.

Wahle, Andreas et al "Accurate Visualization and Quantification of Coronary Vasculature by 3-D/4-D Fusion from Biplane Angiography and Intravascular Ultrasound", SPIE Proceedings, vol. 4158, 2001.

* cited by examiner

ULTRASOUND ANALYSIS METHOD AND DEVICE

CROSS-REFERENCE TO PRIOR APPLICATIONS

This application is the U.S. National Phase application under 35 U.S.C. § 371 of International Application No. PCT/EP2020/053841, filed on Feb. 14, 2020, which claims the benefit of European Patent Application No. 19290011.6, filed on Feb. 14, 2019. These applications are hereby incorporated by reference herein.

FIELD OF THE INVENTION

The present invention relates to an ultrasound processing method and device, in particular for detecting the presence of objects in intravascular ultrasound data.

BACKGROUND OF THE INVENTION

Intravascular Ultrasound (IVUS) imaging is a valuable technique to obtain internal images of the cardiovascular system of a patient, such as the patient's arteries or heart. The IVUS images may assist in assessing a condition of the cardiovascular system, such as for example in detecting and quantifying the size of a stenosis, the build-up of plaque, or in assisting with the positioning of a medical implant such as a stent.

In order to obtain the IVUS images, a minimally invasive medical device such as a catheter or guidewire fitted with an ultrasound probe or set of ultrasound transducers, e.g. at its tip, is inserted into the cardiovascular system of the patient, typically into an artery, after which the IVUS images are captured at regular intervals whilst pulling back the minimally invasive medical device. In this manner, captured cross-sectional IVUS images of the cardiovascular system can assist in providing valuable insights into the condition of the cardiovascular system along its imaged length.

IVUS devices e.g. catheters incorporate one or more ultrasound transducers for imaging the vessel lumen.

The transducers emit and receive ultrasonic energy in order to create an image of the vessel of interest. Ultrasonic waves are partially reflected by discontinuities arising from tissue structures such as the various layers of the vessel wall, red blood cells, and other features of interest, including artificial objects implanted into the vessel.

Echoes from the reflected waves are received by a transducer and passed to an IVUS imaging system, which may for instance be connected to the IVUS catheter by way of a patient interface module termed a "PIM". The imaging system processes the received ultrasound signals to produce e.g. a cross-sectional image of the vessel.

Two types of IVUS catheters are commonly in use today: rotational and solid-state. For a typical rotational IVUS catheter, one or more ultrasound transducer elements are located at the tip of a flexible driveshaft that spins inside a sheath inserted into the vessel of interest.

In contrast, solid-state IVUS catheters carry an ultrasound scanner assembly that includes an array of ultrasound transducers, such as a one-dimensional or two-dimensional array, distributed around the circumference of the device and connected to a set of transducer control circuits. The array and its corresponding circuitry are often referred to as the imaging core or scanner of the IVUS device.

For traditional image generation, transducer control circuits may select individual or groups of transducers of the array for transmitting an ultrasound pulse and/or for receiving the echo signal. By stepping through a sequence of transmitter-receiver pairs, sequentially around the circumference of the device, the IVUS system can synthesize the effect of a mechanically rotating transducer element but without moving parts. Since there is no rotating mechanical element, the transducer array can be placed in direct contact with the blood and vessel tissue with minimal risk of vessel trauma.

The data captured at each of the sequential positions around the device circumference are often referred to a radial scan lines.

The common way to visualize a full pullback (pullback of the IVUS device along the longitudinal axis of a vessel lumen) IVUS dataset is to display one or more cross-sectional views along the pullback (longitudinal) axis. A cross-sectional view means a representation of the data of a single radial line, along the whole longitudinal pull-back distance. This is illustrated in FIG. 1.

FIG. 1 schematically illustrates an example IVUS device 12 having an elongate device body 14. The elongate device body extends along a longitudinal axis, the direction of which is indicated by line A-A' in FIG. 1. The example IVUS device is shown comprising an array 16 of outward-facing ultrasound transducer elements 20, extending circumferentially around the device. FIG. 1 illustrates activation of one transducer element to generate a single radial acoustic signal line 24 along a particular azimuth angle, $\varphi$, directionality, i.e. along a particular rotational angle $\varphi$ around the device. The single radial signal line 24 captures a single radial line of ultrasound data. Multiple radial signal lines together form a full cross-sectional IVUS image 25.

In FIG. 1, trajectories of two example radial lines, $a_1$ and $a_2$, are schematically illustrated. The corresponding trajectories of the lines within the full IVUS scan image 25 are also shown.

Although a single transducer element is shown as generating each radial line, in practice, each radial scan line may be generated using a subset of transducer elements (to enable beamforming to be used to focus an acoustic transmission and reflection along a single narrow radial axis). The subset may comprise for instance up to 14 transducer elements that are circumferentially or azimuthally aligned. Furthermore, array 16 may in some examples comprise multiple elements in the longitudinal direction along A-A' (i.e. have multiple columns).

By way of example, in one known implementation, the array of transducer elements is only element wide in the longitudinal direction and has 64 elements in the azimuthal, $\varphi$, direction. A subset of 14 transducer elements is used to create 4 radial rays. Indexing the active subset azimuthally through the 64 element positions results in the composition of 4×64=256 radial rays per IVUS frame. These figures represent only one exemplary implementation and are not limiting.

In operation, the device 12 is pulled back longitudinally along the vessel 28 lumen in which it is inserted. This is illustrated in FIG. 2. The device steps circumferentially through sequential transducer elements 20 (or sequential azimuthal subsets of transducer elements), each transducer element (or subset) capturing a different respective radial line of ultrasound data. Each complete circumferential cycle of the radial lines constitutes data for a single frame, f. The longitudinal pulling of the device 12 means that sequential frames of data, f, correspond to sequentially advancing longitudinal positions along the vessel 28 lumen as illustrated by the arrow in FIG. 2.

FIG. 3 (top) shows a sequence of reconstructed IVUS frames as well as a cross-sectional view (FIG. 3, bottom). Each IVUS frame represents a full radial cross section, along a sectional plane parallel with the radial axes of the IVUS device and perpendicular to the longitudinal axis. Each radial IVUS frame is composed of the data for a full set of radial lines around the whole set of azimuthal (rotational) angular directions around the IVUS device.

The cross-sectional view shown at the bottom of FIG. 3 represents a cross-section along a sectional plane parallel with the longitudinal axis of the IVUS device and parallel also with the particular (vertical) radial axis shown in the images.

The depicted IVUS frames are 100 frames apart. The overlaid arrow indicates the location and direction of the cross-section in each case. In the bottom cross-sectional view, the column that corresponds to each frame is indicated by the corresponding four arrows. Note that, while the $2^{nd}$ through the $4^{th}$ frame contain a stent, the stent presence is poorly visible in the cross-sectional view and similarly poorly detectable from this cross-sectional view.

A challenge with IVUS is that, due to the multiple dimensions of data collection, it is difficult to represent or treat the data in a manner that provides useful or intuitive results for users. Current approaches typically represent data as single cross-sectional planes across the vessel or along its length such as that shown in FIG. 3. These can only represent a small section of the vessel wall at a time. Because only a subset of the volume is visible at a time, features such as blood vessel side branches may be missed during analysis. This is important in the case of implantation of a stent (or other intravascular object) since the ultimate positions of the stent borders should preferably not overlap with side branches.

In addition, if looking to inspect an object which has been implanted, or seeking to identify proximal and distal edges of an object such as a stent during implantation, this is can be made difficult when the full inner circumference of the vessel across its length cannot be analyzed or inspected at once.

Improved approaches to IVUS ultrasound data treatment are therefore sought.

SUMMARY OF THE INVENTION

The invention is defined by the claims.

According to examples in accordance with an aspect of the invention, there is provided an ultrasound data analysis method for analyzing ultrasound data captured by an intravascular ultrasound, IVUS, device, the method comprising:
  receiving a plurality of frames of ultrasound data captured by an IVUS device, each frame comprising data for a plurality of radial scan lines, each radial scan line corresponding to an acoustic signal reflection along a direction of a different rotational angle ($\varphi$) with respect to a longitudinal axis (A-A') of the device;
  processing the ultrasound data for each radial scan line in each frame, to reduce the data for each line to a single representative data value for the line;
  deriving from the set of representative data values a set of probability values corresponding to probability of presence of an artificial intravascular object at least within each frame;
  determining a region within the ultrasound data occupied by an artificial intravascular object based on the probability values.

Embodiments of the invention are based on permitting easier analysis and treatment of data, as well as more intuitive presentation of the data, by condensing data for each whole scan line into a single representative value or number, such as for instance maximum pixel intensity along the scan line or its standard deviation. This allows a whole line of data to instead be treated as a single point, greatly reducing the complexity of processing operations for identifying objects within the data.

Embodiments of the invention are based on the insight that for detection of intravascular objects, especially artificial intravascular objects, the whole radial scan line of data is not needed, since the object will typically induce some notable contrast or variability in a certain characteristic in the data at the localized area within which it is located. For instance intensity may be detectably higher or lower at the particular region occupied by the object.

As well as faster and simpler processing of data to identify objects, embodiments of the invention offer the advantage that an overview of an entire pull-back intravascular scan can be presented in one single 2D map, or only a small number of 2D maps, as the set or sets of representative points, plotted against azimuth or rotational angle ($\varphi$) of the radial line on one axis, and frame number on the other axis. The data presented in this map may be the most relevant data for detecting presence of objects.

The representative values may in examples contain information relating to or indicative of a spread or range of data values in a given line, for instance a maximum or peak data value in the line, a minimum data value in the line, or a standard deviation or variance of data values. The data values may be intensity.

Presence of an object within a particular scan line, or within a particular frame, may be detected in some examples by looking for one or more contrast or variability properties of the data in each line (a single value) rather than processing a whole set of visual data and searching for an object. The representative values may correspond to such a contrast or variability property for each line.

Contrast or variability properties might include for instance a standard deviation of intensity values for a single radial line, or for instance a maximum intensity point of a line. For instance a maximum intensity value or intensity standard deviation for a line, or set of lines, which is higher than certain surrounding or neighboring lines may indicate (at least a high probability that) an object is present in that line or set of lines. These may indicate boundaries or edges of an object.

More generally, the representative value may relate to a representation of intensity values of the respective radial line.

Embodiments of the invention may be for determining a region within the ultrasound data occupied by an artificial (foreign or "man-made") intravascular object, such as, by way of non-limiting example, a stent, a sheath, and/or a guide-wire. These tend to generate relatively large reflections, which produce characteristic patterns of high intensity at localized regions in the ultrasound data. The region occupied by the object may be identified in the data at least in part based on detection of such patterns within the data.

Additionally or alternatively embodiments may in some examples be for determining a region within the data occupied by an anatomical structure or feature such as, by way of non-limiting example, vascular bifurcations (where a blood vessel divides into two branches), and vascular side-branches. Additionally or alternatively, embodiments may in some examples be for determining a region within the data occupied by a pathology, such as, by way of non-limiting example, plaque, calcifications, or areas of thrombosis.

More than one region may be detected in certain examples. The method may comprise detecting at least one region in the data occupied by an intravascular object.

As noted above, during collection of the data, the IVUS device is pulled through a body lumen e.g. a blood vessel lumen, with frames being captured at regular intervals. This results in a dataset comprising a plurality of frames, each corresponding to a different longitudinal position along the lumen. Each frame includes data for each of the radial lines. Hence the frame number corresponds to longitudinal position, and the radial line number corresponds to circumferential position.

Azimuth angle means the rotational angle about the longitudinal axis of the IVUS device. It corresponds to the azimuth angle co-ordinate in a standard cylindrical co-ordinate system.

The method may further comprise generating a data output representative of the determined region within the ultrasound data occupied by the artificial intravascular object.

Determining the region occupied by the intravascular object may comprise identifying a consecutive subset of frames of the data occupied by the object, and/or identifying a consecutive subset of radial lines occupied by the object. An object will typically occupy a series of frames (due to its longitudinal extension) and/or a series of radial lines (due to its circumferential extension), and hence a region within the data occupied by the object may comprise a consecutive series of frames and/or a consecutive series of radial lines.

Determining the region occupied by the object based on the probability values may be done in different ways.

According to some embodiments, the determining the region may comprise detecting edges of the intravascular object. Edges may manifest as areas of high contrast in the data, for instance a rapid change in intensity values as the region of the object is entered, making them relatively straightforward to detect. Edges in some cases generate characteristic patterns or characteristic changes in patterns in the data which allows them to be detected.

For example, an edge may be detected based on detecting a step change in the probability values (for instance between two consecutive frames or across a subset of frames), or based on detecting a drop or rise in the probability of a pre-defined steepness/gradient.

A (longitudinal) proximal and distal edge of the object may be detected. These may occupy different frames, separated by the region occupied by the object.

According to at least one set of embodiments, the determining the region occupied by the intravascular object may comprise identifying a consecutive subset of frames for which the derived probability values are all higher than a pre-defined threshold.

The threshold may in specific examples be 50%, or approximately 50%. The threshold value may in some examples be dynamically set dependent on the context, or specified by a user for instance.

This approach is computationally simple, meaning it can be performed very quickly and with relatively low processing power and resource. It may comprise for instance application of a simple temporal filtering operation with for instance a rectangular filter kernel that is applied to the temporal sequence of probability values.

A variation on this approach may comprise identifying the largest consecutive set of frames having a probability value above the pre-defined threshold. This would take into account that more than one region may exist that meets the criterion, and would apply the assumption that the largest such region is the one most likely to be truly occupied by an object. This may increase robustness and reliability of the method.

A minimum length for the consecutive set of frames may be imposed in some examples to filter out false positive results caused by noise for instance.

A further variation may comprise applying a dynamic process of identifying the longest consecutive set of frames having the highest probability value, i.e. an optimization process between length and probability. This may be an algorithm which applies different weightings to probability value versus length of subset to identify the most likely region of occupation.

According to at least one set of embodiments, the determining the region within the data occupied by the intravascular object may comprise testing a plurality of trial regions of occupation within the data. The testing may comprise calculating for each trial region a difference between the set of probability values for the trial region and an equivalent set of probability values representative of exact occupation of the region by an object. Exact may mean certain.

For example, the set of probability values for the trial region may be compared to a test probability curve or function or waveform representative of assumed occupation of the region by an object. This may comprise a simple square signal having a probability height of 1, and a width or extension corresponding to the extent of the trial region.

This approach is more robust and may produce more reliable results that the simpler threshold approach outlined above.

The testing may comprise evaluating a cost function for each trial region.

Exact occupation may comprise probability values of 1 across the whole region.

The testing may in examples comprise calculating a cost function, the cost function comprising as at least a first additive term the sum of said set of difference values mentioned above for the whole set of frames across the trial region.

The cost function may comprise as a further additive term a sum of the probability values for consecutive sets of frames on one or both sides of the trial region.

According to any embodiment of the invention, the representative values may be representative of a maximum intensity value for each radial line, i.e. the representative value for each line is representative of the maximum intensity value for that line. They may hence each correspond to the value of the maximum intensity point along the line. This process results in a two-dimensional map of intensity values as of function of radial scan line index and of frame index, and is sometimes referred to as a maximum intensity projection.

Maximum intensity values are ideally suited for the purposes of object presence detection due to the fact that objects tend to generate characteristically high intensity regions across the area of the data within which they are located. Hence, the maximum intensity value of each line essentially corresponds to a rough indicator of presence or absence of an object. If the maximum intensity is above a certain characteristic threshold for instance, this may be an indication that an object is present somewhere in the line.

The method may further comprise analyzing the set of maximum intensity values for the whole set of lines and whole set of frames to thereby detect location of an object presence. This may comprise for instance identifying the points where high values drop to lower values. These points may be taken as indicative of locations of edges of an object in some examples.

According to certain advantageous examples, the method may further comprise determining a set of index values representative of the location of each identified maximum intensity value along each radial line. Due to the orientation of the radial line projection, this may correspond to a longitudinal position of the maximum intensity point. This allows the longitudinal location of an object along the vessel lumen to be more precisely identified.

Maximum intensity represents just one advantageous example. Other example representative values include, by way of non-limiting example, standard deviation of the intensity values in each line, an index representative of a location along the line at which a maximum intensity point is found, an index representative of the location along the line at which a first pixel exceeding a pre-defined threshold is found, or any other suitable example. Further examples will be discussed in the subsequent section of this disclosure.

According to one or more embodiments, the method may comprise generating a plot or map of the representative values, for example a plot or map representing the values against frame number and/or radial line number. This plot or map may be communicated as a control output to an associated display device, for displaying the plot or map to a user for example. The plot or map may show the representative values plotted against at least radial line number along one axis.

According to one or more examples, the deriving the probability values may comprise detecting within the set of representative values one or more characteristic patterns, characteristic of presence of an object.

For example, the method may comprise detecting patterns in the frame-wise sequence of probability values, meaning the sequence of probability values over consecutive incrementing frames.

For example, the method may comprise detecting patterns in the spread or distribution or variation of the values as a function of incrementing frame number and/or radial line number.

The characteristic patterns to be detected may be pre-determined, for instance pre-stored in advance.

In some examples, the characteristic pattern may comprise a consistent region of high intensity values, or high maximum intensity values.

In some examples, the characteristic pattern may be a pattern indicative of an edge of an object, for instance a rapid, e.g. step, change in intensity values, or in maximum intensity values. In some examples, the characteristic pattern may comprise a castellated (up and down or undulating) pattern in the representative values.

According to one or more examples, the deriving the probability values may comprise use of a classifier algorithm.

The classifier algorithm may comprise a machine learning algorithm. The machine learning algorithm may be trained using labelled or annotated training data comprising multiple example sets of probability values, each labelled to indicate whether an object is present or not present. Using this training data, the algorithm may learn to distinguish, i.e. classify, sets of probability values indicative of object presence and sets of values indicative of no object presence.

In some examples, the algorithm may be a neural network.

In other examples the algorithm may comprise a random forest (RF) algorithm. In this case, the deriving of the probability values may further comprise use of a wavelet transform to perform an initial transform of the aforementioned representative values, with the RF algorithm using the wavelet coefficients to perform the generation of a probability value estimate describing the possible presence of an object in the associated frame or frame range.

According to any embodiment of the invention, each frame may correspond to a different longitudinal location along a lumen. This results from the manner in which IVUS data is collected, by pulling the IVUS device longitudinally through the vessel lumen, capturing successive frames at regular intervals along the way.

Examples in accordance with a further aspect of the invention provide an ultrasound data processor for analyzing ultrasound data captured by an IVUS device, the processor adapted to:

receive a plurality of frames of ultrasound data captured by the IVUS device, each frame comprising data for a plurality of radial scan lines, each radial scan line corresponding to an acoustic reflection along a different rotational angle ($\varphi$) with respect to a longitudinal axis (A-A') of the device;

process the ultrasound data for each radial scan line in each frame, to reduce the data for each line to a single representative data value for the line;

derive from the set of representative data values a set of probability values corresponding to probability of presence of an artificial intravascular object at least within each frame;

determine a region within the ultrasound data occupied by an intravascular object based on the probability values.

Implementation options and details for each of the steps performed by the above processor device may be understood and interpreted in accordance with the explanations and descriptions provided above in respect of the method aspect of the present invention.

Any of the examples, options or embodiment features or details described above in respect of the data analysis method may be applied or combined or incorporated mutatis mutandis into the present device (processor) aspect of the invention.

Examples in accordance with a further aspect of the invention provide an ultrasound system comprising:

an intravascular ultrasound, IVUS, device for capturing ultrasound data within a blood vessel lumen along a plurality of different radial scan lines; and an ultrasound data processor in accordance with any example or embodiment outlined above or described below, or in accordance with any claim of this application, operably coupled with the intravascular ultrasound device, and configured to receive ultrasound data captured by the IVUS device.

The IVUS device may for instance comprise an intravascular probe, for instance a catheter or guidewire.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
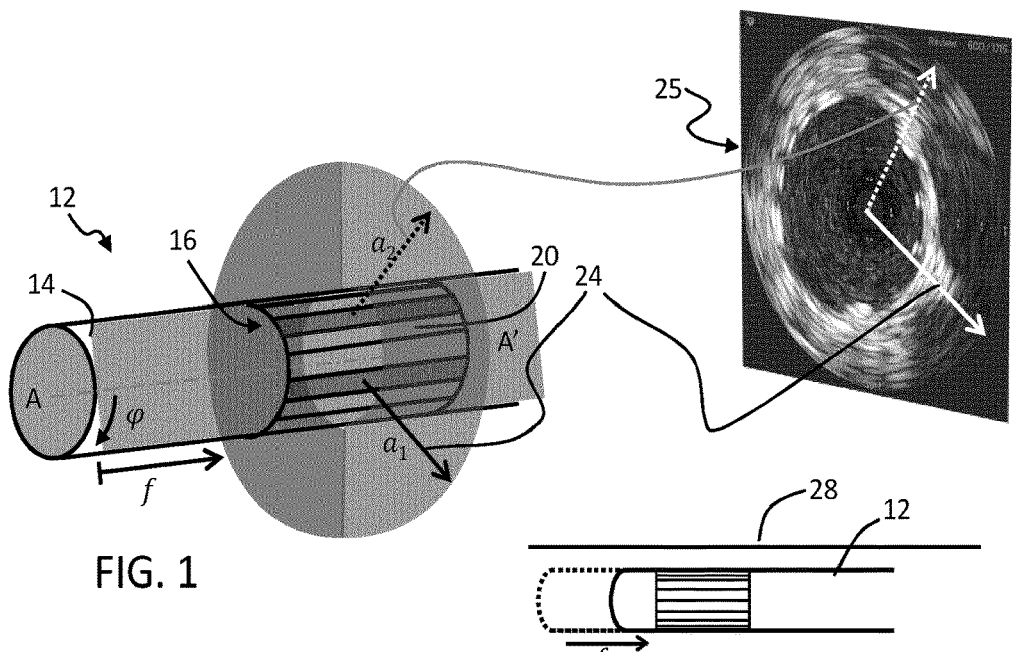
FIG. 1 depicts an example IVUS device, and illustrates capturing of one example radial scan line.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. The same reference numerals are used throughout the Figures to indicate the same or similar parts.

The invention provides an ultrasound data processing method for detecting presence of an intravascular object in a vessel lumen based on analysis of acquired intravascular ultrasound data of the lumen. The method comprises receiving data comprising multiple frames, and each frame containing data for a plurality of radial lines, corresponding to different circumferential positions around the IVUS device body, and reducing the data to a single representative value for each radial line in each frame. These representative values are subsequently processed to derive values for at least each frame representative of a probability of presence of an object within the given frame. Based on the probability values, a region within the data occupied by an intravascular object, for instance a consecutive set of frames occupied by an object, is determined.

Hence the method provides detection of an object within a vein or artery or other bodily lumen, and uses a novel approach whereby data for each line is condensed to a single value to allow faster and easier processing. It may also allow easier representation of captured data for users. The approach is based on the insight that for the purpose of detecting an object, a single representative value for each line provides sufficient information, due to the fact that objects manifest in ultrasound data as regions which contrast with surrounding regions, for instance in terms of intensity values. A single value can therefore capture a degree of variance or spread of data values in a radial line, or a maximum intensity point of a line, where this by itself, in combination with similar values for the other lines in the frame, may provide information sufficient for detecting whether an object is present in that frame of data.

Hence, embodiments of the present invention are based on use of a different representation or treatment of the data, which offers an overview of the intravascular scan in all directions.

Embodiments of the invention propose to apply this simplified treatment of the data for detection and/or classification of intravascular objects, particularly artificial intravascular objects, which tend to generate large reflections in the data, allowing them to be identified through searching for certain contrast properties in data for example.

The use of this treatment of data for detection of intravascular objects, anatomical structures or pathologies is not known in the art. Examples of artificial intravascular objects include, by way of non-limiting example, stents, sheaths and guidewires. Examples of anatomical structures include, by way of non-limiting example, bifurcations. Examples of pathologies include by way of non-limiting example, plaque, calcifications and thrombose.

Figure 4:
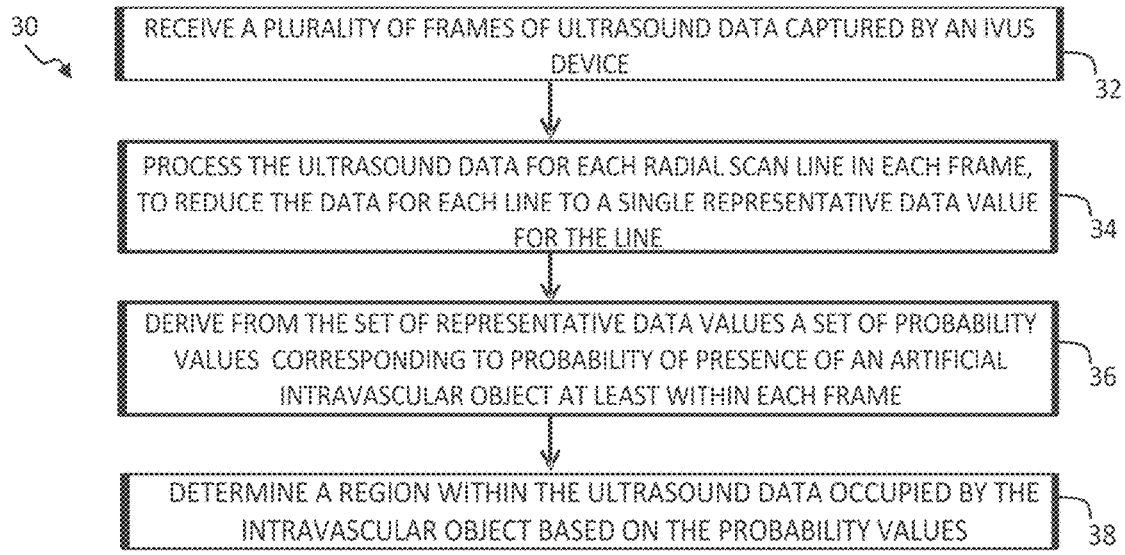
FIG. 4 shows an example data analysis method according to one or more embodiments.

FIG. 4 shows in block diagram form an example ultrasound data analysis method 30 in accordance with one or more embodiments of the invention. The method 30 is for analyzing ultrasound data captured by an intravascular ultrasound, IVUS, device.

The method 30 comprises receiving 32 a plurality of frames of ultrasound data captured by an IVUS device, where each frame comprises data for a plurality of radial scan lines. Each radial scan line corresponds to the received the ultrasound signal along a different radial axis of the device, having a particular rotational (or azimuth) angle, φ, directionality around the device, i.e. a signal received along a different rotational angle, φ, around the body of the device with respect to a longitudinal axis (A-A') of the device. This can be seen more clearly in FIG. 1, as will be explained below. The direction of the longitudinal axis is indicated by line A-A' in FIG. 1.

The data may be received for example from an IVUS ultrasound device. Alternatively, it may be received from a communicatively coupled data-store or memory, or from an external or remote computer or server in certain examples.

The method 30 further comprises processing 34 the ultrasound data for each radial scan line in each frame, to reduce the data for each line to a single representative data value for the line. More than one representative value may be generated in some examples, each representative of the whole radial line.

The method 30 further comprises deriving 36 from the set of representative data values a set of probability values corresponding to probability of presence of an artificial intravascular object at least within each frame.

The method 30 further comprises determining 38 a region within the ultrasound data occupied by an intravascular object based on the probability values.

The method may in certain examples further comprise generating a data output representative of the determined region occupied by the intravascular object, for instance for communicating to an external device, such as an external computer, or for communicating to a patient monitor device or a display device. A control output may be generated for controlling an operatively coupled display device to display the result of the object detection.

The invention is for analysis of intravascular ultrasound (IVUS) data, meaning data which has been captured by an IVUS device 12. As discussed above (see e.g. FIG. 1), an IVUS device typically has an elongate device body 14 and in operation is pulled longitudinally through a blood vessel capturing frames at regular intervals. An IVUS device typically comprises an array 16 of ultrasound transducer elements 20 at its outer surface, extending circumferentially around the device. The signals received by one or more transducer elements after an ultrasonic signal transmission from one or more transducer elements is combined to create one of multiple radial lines of ultrasound data 24. The radial lines of ultrasound data 24 may be combined to form one of multiple frames 25, each of which represents a local spatial slice of the imaged lumen.

Each radial line may be captured by transmitting an ultrasound signal (e.g. an ultrasound beam) along a particular radial axis of the device, having a particular azimuth directionality, φ, meaning along a direction of a particular rotational angle, φ, around the device. The reflected signal is then received and provides the radial line of data. Each radial line may be generated by transmitting an ultrasound beam or ray along the respective radial axis. Each radial line may be transmitted and/or received using a subset of multiple transducer elements, in order to facilitate beamforming for example.

Figure 2:
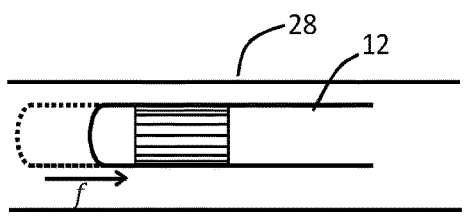
FIG. 2 shows an IVUS device inside a vessel lumen.
Figure 3:
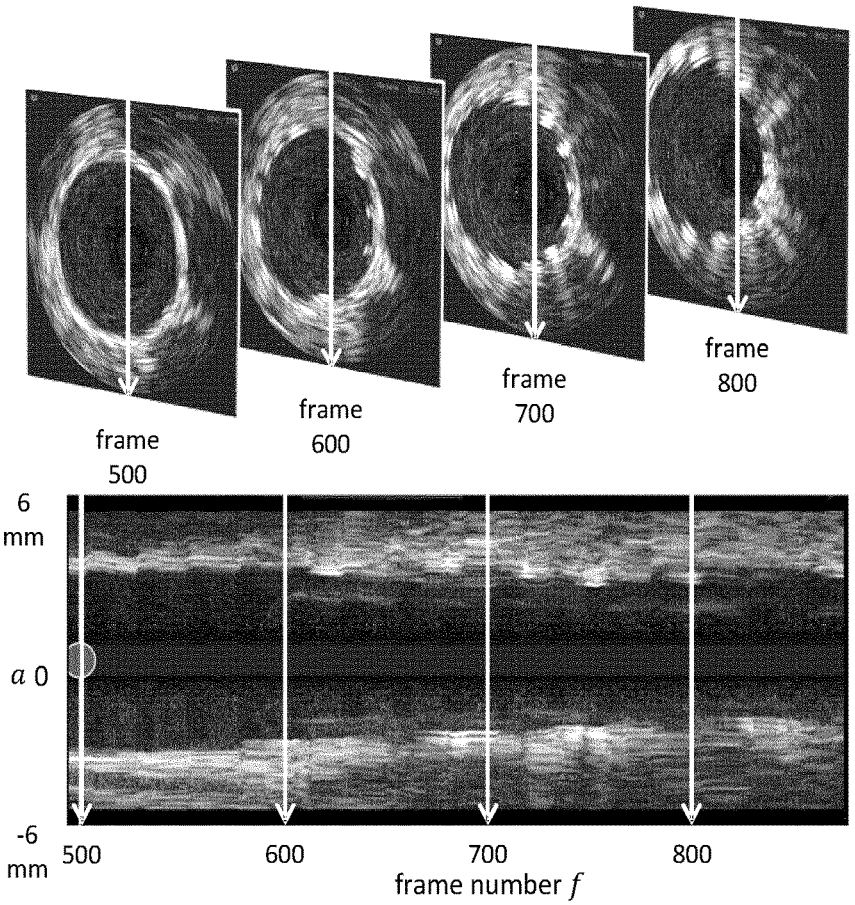
FIG. 3 shows an example longitudinal cross-section as generated in known approaches from IVUS data.

In operation, the device 12 is pulled back longitudinally along the vessel 28 lumen in which it inserted. This is illustrated in FIG. 2. The device steps circumferentially through the array of transducer elements 20, each transducer element (or subset of elements) around the circumference capturing a different respective radial line of ultrasound data. Each complete circumferential sweep of the radial lines constitutes data for a single frame, f.

According to the present invention, the data for each radial scan line 24 is converted to a single representative number, such as maximum pixel intensity or its standard deviation.

Figure 5:
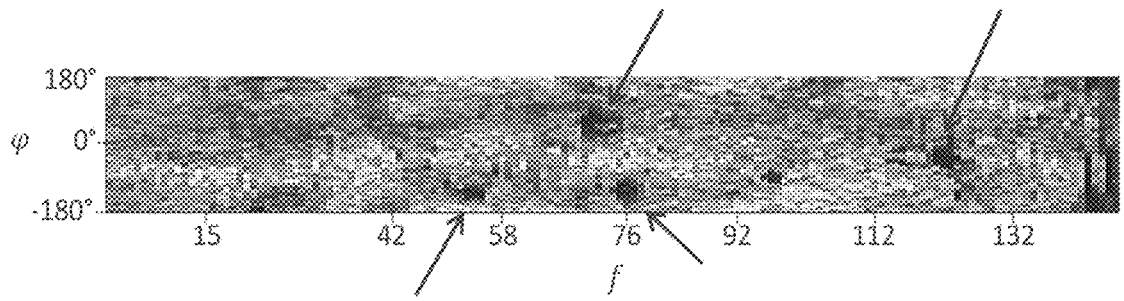
FIG. 5 shows an example 2D map of the interior of a blood vessel, as may be generated in accordance with one or more embodiments.

These values may be plotted in a 2D map. An example is shown in FIG. 5.

The y-axis of the map is azimuth (or rotation) angle, φ, of the respective radial line, and the x-axis is the frame number within which the radial line is contained. Frame number effectively corresponds to longitudinal position along the lumen, due to the manner in which the device is pulled longitudinally along the lumen while successive frames are captured. This is hence a map of representative values (in this example, maximum intensity values) at each circumferential location around the device, at each of a series of longitudinal positions along the lumen.

Such a map may be useful in itself for presentation to a user, e.g. a clinician. For example, vascular side branches show up in this map as dark areas (indicated by arrows in FIG. 5). By contrast, calcifications can be detected as characteristic bright regions within the data. Note that no explicit segmentation of the data is required to be performed, since the map provides an intuitive view of the inside of the vessel, with longitude vs azimuthal angle.

Figure 6:
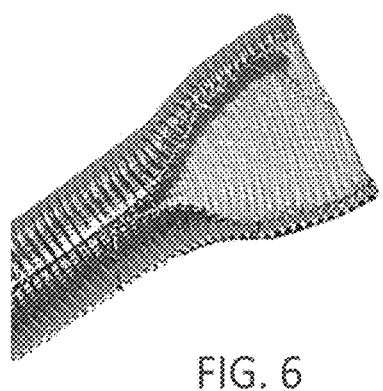
FIG. 6 schematically demonstrates the geometric viewpoint of the interior of the vessel provided by the plot of FIG. 5.

The resulting reduced dataset, when presented as a 2D map, effectively provides an unfolded view of the interior wall of the imaged vessel, as if it were cut along its length and laid flat with the inner face showing, for instance as schematically illustrated in FIG. 6.

For each radial scanline, a representative value of the received ultrasound signal for the whole line is calculated.

By way of non-limiting example, the representative values may for instance include any one or more of the following:

Standard deviation (or variance) of the data values (e.g. intensity values) of the radial line.

Maximum value (e.g. intensity value) of the radial line.

Minimum value (e.g. intensity value) of the radial line.

An index representative of a location of the maximum data value along the line, i.e. a radial position of the maximum value along the line.

An index representative of the data value, or the (e.g. radial) location along the line of, the first pixel along the line having a value exceeding a predefined threshold. The data values may be intensity values.

An index representative of the location (e.g. radial location) along the line at which the cumulative sum of the data values reaches a pre-defined defined percentage (e.g. 75%) of the total sum of the line data values.

The output of a matched filter, having a filter kernel matching the characteristic shape of a target object to be detected. The matched filter will therefore produce an output signal that adopts a (local) maximum value where the target object is present. As such the matched filter may e.g. match the size and/or shape of a stent strut in the radial direction.

At least some embodiments of the invention are for identifying presence of artificial intravascular objects within the ultrasound data. One example of an artificial intravascular object which may be detected in some examples is an intravascular stent.

A vascular stent is typically formed of a tubular length of metal mesh, where the connecting elements of the mesh extending around its circumference are known as struts.

The metal stent struts generate a strong reflection of the incident ultrasound signal. This causes a high maximum in the intensity values and/or a large variance of the intensity values along the radial scan line containing the strut. Where the set of representative values correspond to maximum intensity values or variance values for each line therefore, the location of a strut is detectable in the data as a region of relative high representative values (relative to surrounding values) i.e. an area of high contrast from surrounding values.

Figure 7:
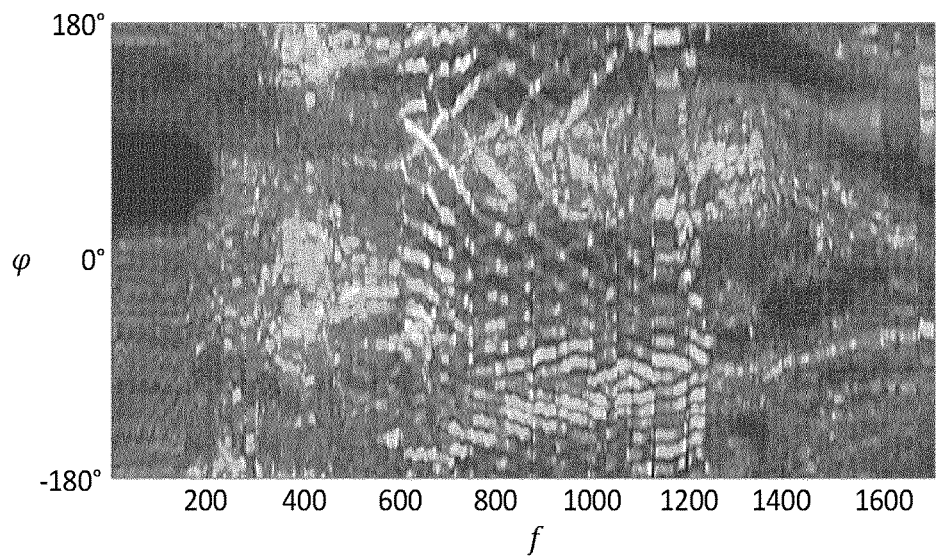
FIG. 7 shows an example plot of maximum intensity values for an example dataset, showing presence of a stent in the data.

This is illustrated in FIG. 7 which shows a 2D map of maximum intensity values for radial lines of an example ultrasound dataset. The illustrated region contains a portion of a stent. The x-axis corresponds to frame number of the scan line, the y-axis corresponds to azimuth angle, φ, of the scan line.

The mesh cross-cross pattern of stents is clearly visible in the data as high contrasting bright areas set against a background of darker values.

The treatment of the data as a set of representative values of each scan line offers advantages over traditional modes of treating and representing captured IVUS data. In typical known approaches, the whole IVUS dataset is used in any analysis procedure, and detection or identification of objects or anatomical regions within the data is performed based on segmentation. The segmentation may make use of anatomical model information, and comprises detecting outlines of identifiable objects, based on reference outlines or images.

However, particularly for intravascular ultrasound, lumen segmentation is unreliable, and highly prone to errors. Hence, the segmentation of the captured data is able to provide only a relatively coarse representation of the vessel wall, in which smaller details such as vascular bifurcations may be easily missed.

The present approach avoids the need for segmentation, by instead simply analyzing the computed representative values, for instance searching for patterns or high contrast regions in the values. Generation of these values in itself performs the process of extracting from the data the key data points most relevant for identification of object presence.

Hence, rather than applying segmentation, embodiments of the present invention follow an approach more common in the field of 3D volume rendering, wherein a 2D output image is composed by directly evaluating the 3D volume along a set of radially directed scan lines. The scan lines extend in a radial depth direction (from the perspective of a generated 2D image of the vessel wall).

This approach allows the presence of even spatially very small details to be identified from the collection of ultrasound data along an entire radial path. For example, in the case of detecting vascular bifurcations, multiple adjacent data points along the same radial path effectively 'cooperate' in creating a local hypo-intense value which is characteristic for such bifurcation.

Figure 8:
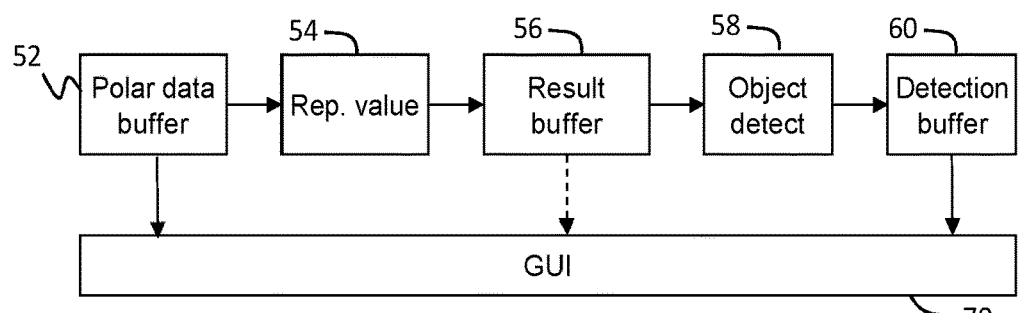
FIG. 8 shows an example workflow for an example method according to one or more embodiments.

An example workflow for an example data analysis method according to one or more embodiments is shown in block diagram form in FIG. 8.

The raw (polar) ultrasound data is first received 52. Optionally, the raw polar data may be output at this point in at least some form to a graphical user interface (GUI) 62 for observation by a user. For instance certain radial lines of data may be output for the complete set of frames. This may be output as a graphical or visual output in some examples.

This is then processed 54 to extract from each radial scan line a single representative value. This comprises performing frame-wise calculation of a representative value per radial A-line (envelope signal after beamforming) within a set of (radial) ultrasound A-lines that together form a single frame. The representative values may provide a contrast mechanism to create a compact representation of data for each frame.

Using representative values which represent data in terms of contrast or variation properties (contrast mechanism) is ideally suited for subsequent detection of object presence. This is because it allows preservation of sufficient information to detect the presence of an object, such as a stent, graft, guiding sheath, guidewire or any other intravascular object, since objects tend to show up as high contrasting areas compared to the background. Hence the approach of embodiments of the present invention follows at least in part from the insight that for at least certain choices of contrast mechanism, the output set of representative values appears to preserve sufficient relevant information to enable successful detection or classification of an object.

The resulting set of representative values is then buffered 56. Optionally, the derived set of representative values may be output at this point to a graphical user interface (GUI) 62, for observation by a user. They may be output in graphical or visual form. For instance, a 2D map or plot of the generated set of representative values, for example as shown in the example 2D map of FIG. 5, may be generated, and a control signal representative of this graphical output communicated to an associated GUI 62 such as a display device or a patient monitor.

An object detection procedure 58 is then applied to the generated set of representative values, which detects whether there is presence of an object in the data, and preferably determines a region occupied by the object within the data. This is based on deriving a set of probability values representative of probability of presence of an object in each frame of the data, and then determining from these values a region occupied by an object within the data.

The result of the detection procedure 58 is then buffered 60. The result of the detection procedure may be output to a graphical user interface 62, for instance in graphical, textual or any other form. Alternatively, the result may instead be stored locally or remotely for instance.

Figure 9:
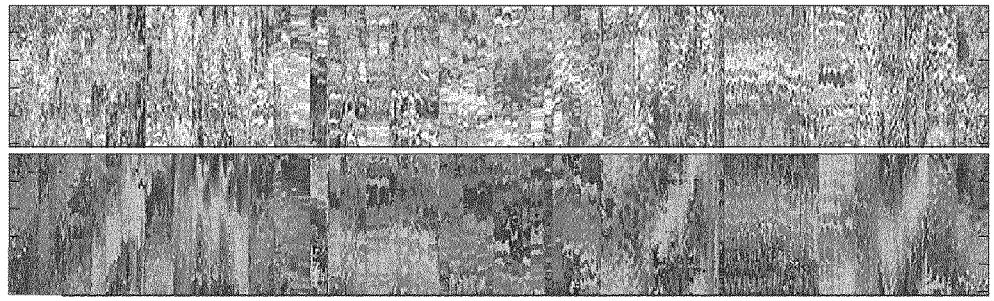
FIGS. 9 and 10 show 2D maps representative of maximum intensity values and maximum intensity index values for radial lines of example datasets, for the cases of object presence and object absence respectively.

A further, more specific, example workflow for an example data analysis method according to one or more embodiments is shown in FIG. 9. In this example, the representative values derived from the ultrasound data are maximum intensity values.

For application to artificial object (e.g. stent) presence detection it has been found that the use of so-called maximum intensity projection (MIP) is a useful representation of line-wise data. MIP is known as a computationally efficient method in 3D volume rendering to visualize volumetric data that is stored as so-called voxel values in a 3D data buffer. When applied to volumetric data, the MIP results in an image which has the appearance of a semi-transparent projection of the 3D volume onto the 2D image plane.

MIP is based on identifying the maximum intensity voxel or pixel along a projection line through the volume data and then using that value for the output 2D MW image.

A similar type of approach is followed in certain embodiments of the present invention, wherein a maximum intensity projection is taken along each radial line. This means that each radial line is converted to a single value corresponding to the maximum intensity value along that radially directed scan line. Hence, effectively, a similar MIP operation is used to transform raw frame-wise 2D ultrasound polar data into a single value (the maximum intensity value).

Furthermore, according to an advantageous set of examples, two representative values are derived for each line: the maximum intensity value itself, and an index representative of a location of that maximum value along the radial scan line (referred to herein as 'maximum intensity index'). Extracting these two pieces of information enables certain more robust object detection procedures to be performed, as will be explained in more detail further below.

The maximum intensity value and the maximum intensity index can be understood as a set of two 1D vectors.

For a given sequence of acquired frames, both the maximum intensity value vectors and the maximum intensity index vectors can each be represented on a respective 2D map, similar to the map of FIG. 5.

Figure 10:
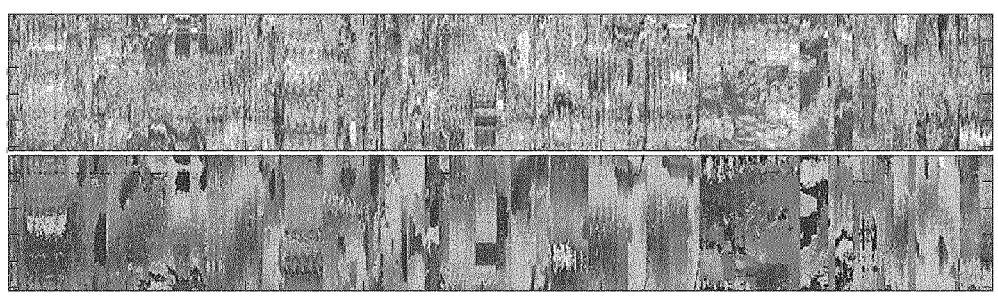

Two examples are shown in FIGS. 9 and 10. The upper map in each figure shows a map of the maximum intensity values for each radial scan line, and the lower map in each figure shows a map of the maximum intensity index values for each radial line. In each case, the values are plotted against azimuth angle of the line on the y axis and frame number on the x-axis. FIG. 9 corresponds to the maximum intensity and index values for a sample set of data in which an object (in particular a stent) is present, and FIG. 10 corresponds to a sample set of data in which an object is not present.

The presence of a stent in FIG. 9 is clearly revealed by a characteristic pattern caused by the crisscrossing mesh arrangement of stent struts. The relatively strong reflections cause a bright local maximum intensity value (upper plot) and the strut spacing causes a distinct castellated pattern in the maximum intensity index values (lower plot).

Figure 11:
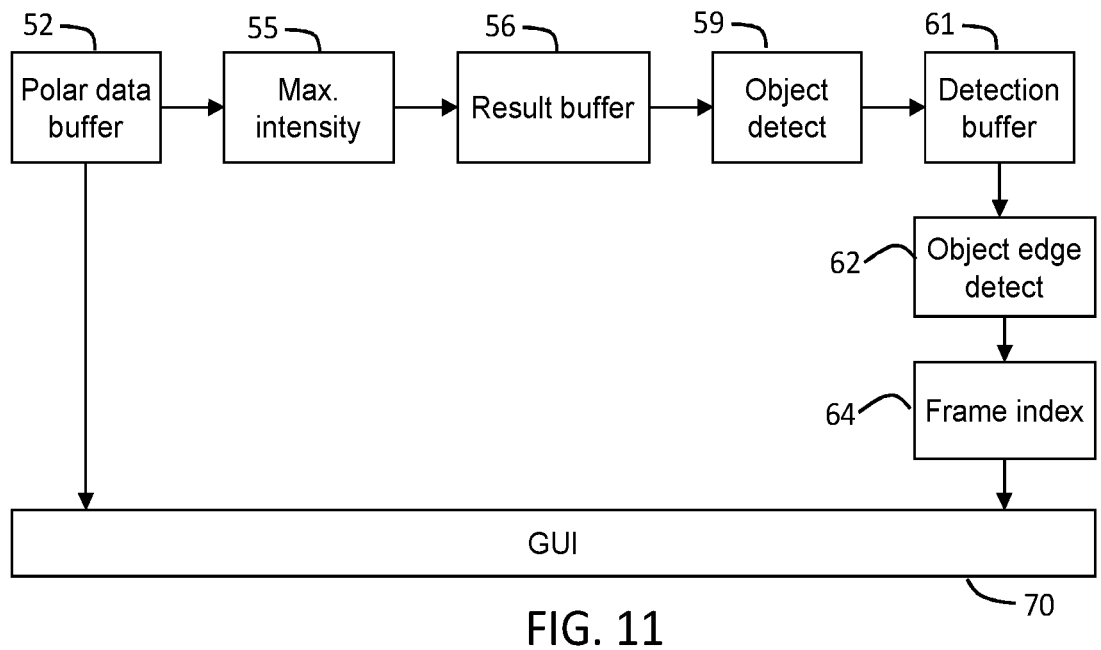
FIG. 11 shows an example workflow for an example method according to one or more embodiments.

FIG. 11 shows an example workflow for an example method which employs extraction of maximum intensity values and maximum intensity indexes.

As in the workflow of FIG. 8, the method comprises receiving raw polar ultrasound data 52. Again, optionally, this may be output at this stage to a graphical user interface (GUI), for instance in a graphical form. The method may comprise rendering a graphical output, or the GUI may perform the rendering.

The method then comprises extracting 55 the maximum intensity values and maximum intensity indexes for each radial scan of the received data. This is then buffered 56.

An object detection procedure 59 is then applied, which comprises detecting whether an object is present in the data or not present.

This may be based on deriving a set of probability values representative of probability of presence of an object in each frame of the data, and then determining from these values whether or not an object is present.

The result of the object detection procedure is then buffered 61.

If an object has been detected, then an edge detection procedure 62 is then applied for determining locations within the data of edges of the object. Again, this may be based on use of a set of probability values derived from the extracted maximum intensity and maximum intensity index values.

This procedure generates as an output the frame indexes (or frame numbers) within which the edges have been found to be located. This may then be output to a user display such as a GUI 70 for presentation to a user.

The edge locations provide an indication in themselves of the region occupied by the object, e.g. the stent. These naturally indicate the region between the two identified edges, i.e. the consecutive set of frames between the two edge location frames.

Example procedures for performing each of the above steps will be described in greater detail below.

Although use of maximum intensity values as the representative value for each radial line is discussed in detail in this example, the invention is not limited to use of this particular type of representative value. In other examples, the data for each scan line may be converted to a different representative value. A number of different example representative values which may be used in accordance with embodiments have been outlined above.

As discussed above, the method comprises deriving from the set of extracted representative values for the radial scan lines, a set of probability values corresponding to probability of presence of an intravascular object, for instance an artificial intravascular object, at least within each frame.

These values may in some examples be temporally averaged or smoothed, to generate a continuous sequence or curve of probability values as a function of frame number. This sequence of probability values may then be processed to detect a region of the data (a set of consecutive frames) which an object is occupying. More than one region may be detected in some examples.

Generation of the probability values from the set of representative values may be performed in different ways. Different example methods for generating the set of probability values will now be outlined in detail. Following this, various example methods for detecting from the probability values presence of an object and determining a region of the object's occupation within the data will be described.

A first example method will be outlined below. This approach is based on deriving maximum intensity values from each radial line as the representative value. For brevity, the maximum intensity values will be referred to a "MIP values".

One example method for converting the frame-wise representative values (e.g. MIP values) into a probability estimate of an object (e.g. a stent) being present in the associated frame is based on use of a random forest (machine learning) classifier algorithm, and a discrete wavelet transform (DWT) to reduce the dimensionality of the input data. This approach preferably uses MIP values as the representative values, and is based in part on the observation that the presence of a stent tends to cause a characteristic pattern of both in the values of the MIP as well as the index of the MIP. This approach has been shown to be less computationally demanding than a second method (described further below) due to the relative simpler algorithm and hence reduced computational complexity.

It is noted that although the below example is described, for illustration, with reference to detection of a stent, this is by way of example only. The approach is not limited to the detection of stents. It may also be used for detection of any other intravascular object, and has for example been successfully tested for use in detection of other vascular inserts such as, but not limited to, a guiding sheath or a vascular graft.

Figure 12:
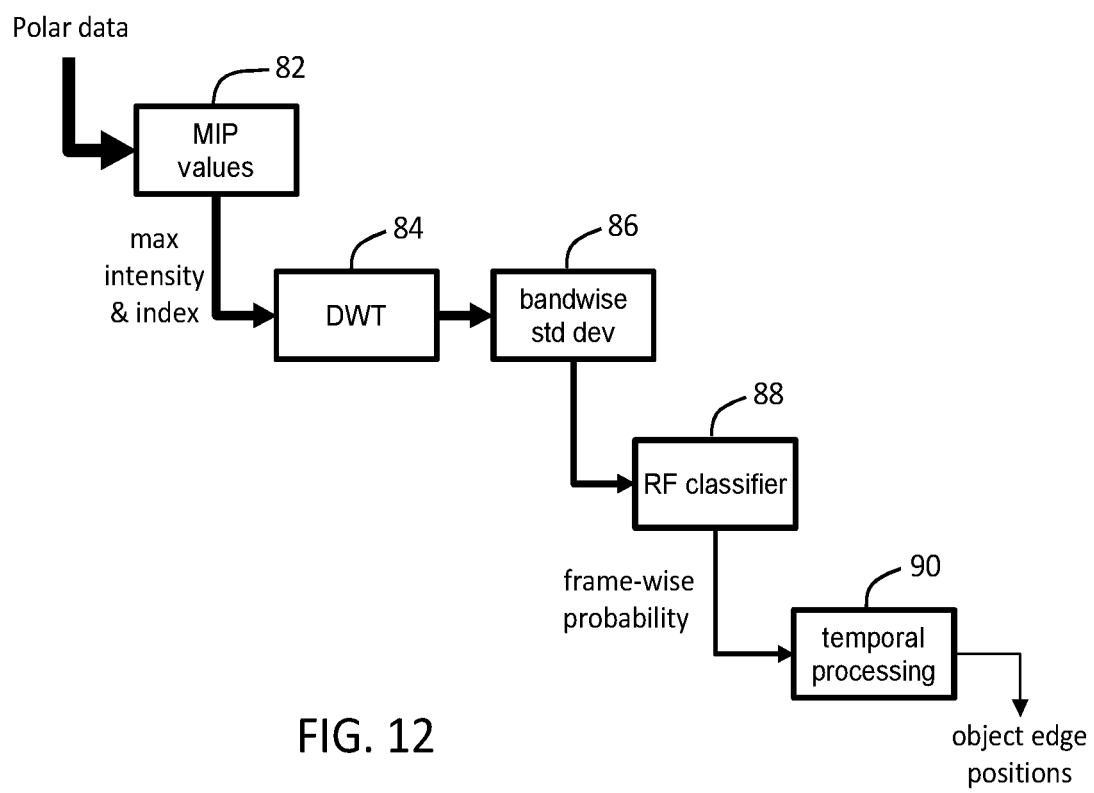
FIG. 12 shows an example workflow for an example procedure for deriving a set of probability values for probability of presence of an object in each data frame.

This approach is based on the combination of a discrete wavelet transform (DWT), a standard-deviation calculation and a random forest (RF) classifier. The workflow of the example method for deriving the probability values is shown in block diagram form in FIG. 12.

First, the full set of IVUS ultrasound data is processed 82 to reduce the data in each radial line to a single representative value in the form of an MIP value, and additionally an accompanying index indicating a location along the respective line at which the maximum intensity value was found.

These output values are then provided as an input to a discrete wavelet transform (DWT) 84. The DWT is used to reduce the dimensionality of the data from 2×256 values to 15 values per frame (corresponding to the 15 radial lines comprised in each frame). These numbers are exemplary only and do not limit the invention.

The discrete wavelet transform process 84 generates as an output a set of the band-wise variances 86 of the resulting wavelet coefficients. These effectively provide a secondary feature vector.

The band-wise variances or standard deviation 86 is then provided as an input to a Random Forest (RF) classifier algorithm 88. This algorithm is trained to produce for each frame a probability value (between 0 and 1) indicating the probability of presence of a stent (or other object) in the respective frame.

The RF classifier may be an algorithm which has been trained on the basis of labeled example data. After training, the algorithm comprises a collection of trained decision trees which in combination can act both as a classifier (presence or no presence in frame) as well as a regressor (regression analysis). The regression function may be configured to produce a continuous probability value or function (or a sequence of values) for the set of frames, each between 0 and 1.

As noted above, presence of an object (e.g. a stent) can be identified within the data based on presence of a characteristic pattern within the data caused by the object. Most artificial objects, such as stents, generate relatively strong reflections which cause a bright local MIP value and the strut spacing causes a distinct castellated pattern in the MIP index. Hence, these distinct patterns provide one means for detecting likely object presence. The classifier algorithm may be trained to detect such patterns or to use such patterns as part of determination of probability of presence of an object within a frame.

The set of probability values may subsequently be temporally averaged or filtered using a frame-wise filtering operation (temporal filtering operation) 90, which results in a sequence of locally temporally averaged probability values. From these, edges of the stent (or other object) may be detected with a suitable edge detection procedure, and thus the region occupied by the object identified. Example procedures for determining the location of the object based on the probability values will be described in detail further below.

As noted above, the approach involves application of a discrete wavelet transform, and generates an output for feeding to the RF classifier comprising a set of band-wise variances of the wavelet coefficients. This procedure will now be discussed in more detail.

The choice for a frequency transform such as the wavelet transform is based on the observation that a pattern of stent (or other object) struts results in a characteristic regular pattern in the set of MIP values (and MW indexes). This pattern is quasi-periodic in its nature. For this reason, the characteristic pattern (indicative of object presence) can be associated with one or more characteristic spatial frequencies.

By way of example, in advantageous examples, a discrete Haar wavelet transform may be used.

Figure 13:
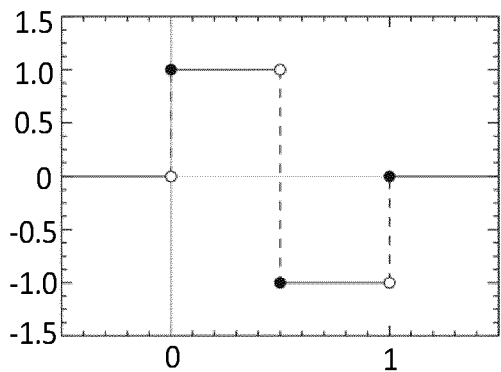
FIG. 13 shows the shape the basis function of a Haar wavelet, as applied in the example procedure of FIG. 12.

The use of a discrete Haar wavelet has advantages in terms of its relatively limited computational complexity, thus making the procedure faster and more computationally efficient to run. This simplicity follows from the square shape of the Haar basis function. This shape is depicted in FIG. 13 for illustration.

The continuous Haar basis wavelet function, $\psi(t)$, has the form:

$$\psi(t) = \begin{cases} 1 & 0 \le t < \frac{1}{2}, \\ -1 & \frac{1}{2} \le t < 1, \\ 0 & \text{otherwise.} \end{cases} \quad (1)$$

The normalized discrete Haar wavelet transform results in consecutive convolutions of the input set of MIP values, with the following filter kernels:

$$h[n] = \left[-\frac{\sqrt{2}}{2}, \frac{\sqrt{2}}{2}\right] \text{ and } g[n] = \left[\frac{\sqrt{2}}{2}, \frac{\sqrt{2}}{2}\right], \quad (2)$$

where high-pass filter h[n] and low-pass filter g[n] iteratively convolve the input (MIP value) signal x[n] in a cascade of filtering and down-sampling operations.

Figure 14:
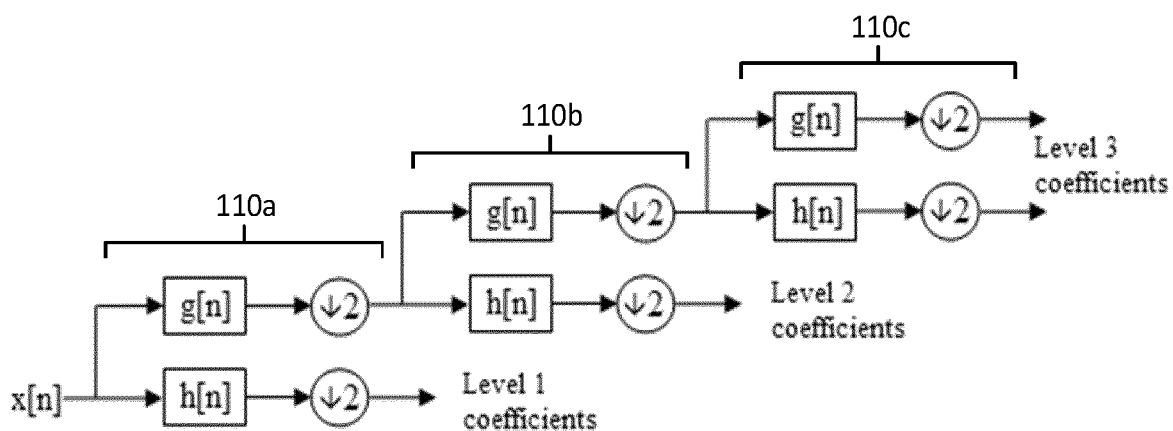
FIG. 14 shows the multiple signal decomposition stages of a wavelet transform applied using the example procedure of FIG. 12.

This cascade of filtering and down-sampling operation is schematically illustrated in FIG. 14. At each decomposition level, 110a, 110b, 110c, the down-sampled low-pass filtered approximation of the signal forms the input for the next signal decomposition. At each level the high-pass and low pass filters, h[n] and g[n] with the kernels outlined above are applied.

For the case of application of the transform to stent-presence detection, the transform may be applied to an input signal x[n], comprising both the MIP values and the MIP indexes. By way of example, a 7-level transform may be applied. This may result in a total of 512 output wavelet coefficients (2×256 wavelet coefficients).

For each sub-band, a standard deviation (or alternatively variance) is calculated to form a vector of 2×7 subband-wise standard deviation values. These values can be understood as spanning a 14 dimensional feature space. These calculated vectors of standard deviation values form the input to the RF classifier algorithm 88.

A second example method for converting the set of representative values for each radial line in each frame into frame-wise stent presence estimations (probability values) is based on the use of one or more convolutional neural network (CNN). Optionally these use the input from multiple frames instead of a single frame. As the neural network is further trained, this approach may become more robust and reliable that the first example approach outlined above. However, it is somewhat more computationally complex.

This approach provides an alternative to use of a wavelet transform. The CNN may for example be trained on the basis of labeled sample data (sample sets of MIP values and optionally also MIP indexes). The algorithm may use deep learning.

In operation, the CNN is fed as an input the frame-wise MIP values, and produces as an output a continuous probability value (or sequence of values) between 0 and 1 of presence in each respective frame of an object.

As such, the use of such a CNN may in certain embodiments replace the combination of discrete wavelet transform DWT, standard deviation calculation and RF classifier, used in the approach above.

Hence, using this Deep Learning approach, the input MIP values (e.g. 2×256 MIP values, using the above example) form the input of the deep convolutional neural network. When trained with representative annotated data, the convolutional neural network can perform the functions of both feature extraction/detection (albeit implicit and hidden) and feature classification. Feature extraction means for instance detecting presence of an object. Feature classification means for instance detecting which object, of a set of possible objects, has been detected.

By feeding the CNN with MIP value data instead of the original full polar data set, the size the neural network can be kept smaller than would otherwise be possible, allowing for a computationally very efficient implementation. Such a small network could feasibly be run in real-time on a typical CPU for example.

Figure 15:
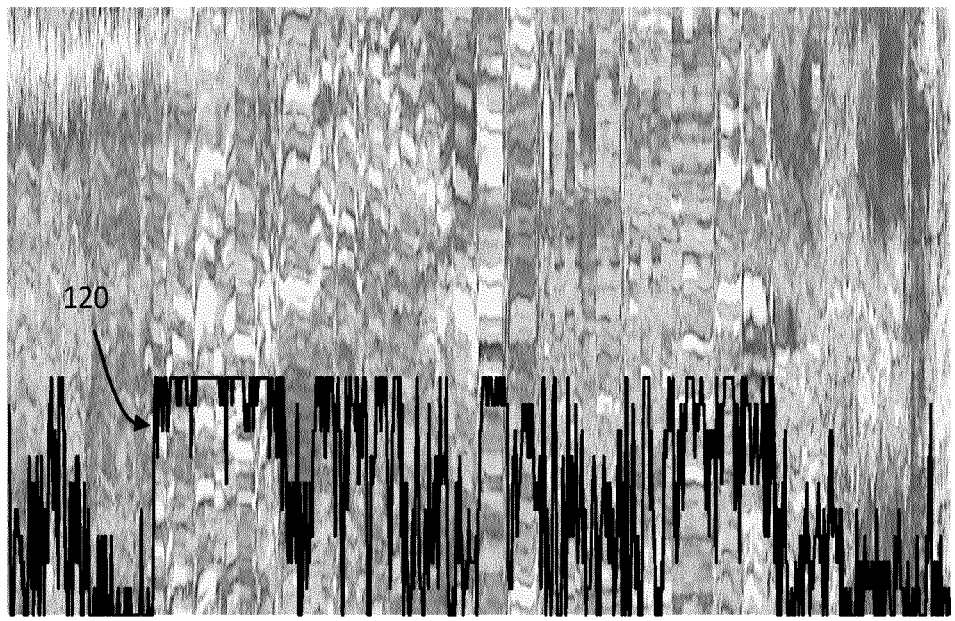
FIG. 15 shows an example set of probability values for frames of an example dataset.

FIG. 15 shows an example of the resulting sequence of frame-wise probability values 120 of object presence in each frame, shown against a backdrop of the maximum intensity values extracted from each of the radial scan lines. The y-axis of the backdrop map corresponds to radial line azimuth angle and the x-axis corresponds to frame number of each radial line.

Each of the above example approaches to deriving the set of probability values comprises use of a machine learning algorithm, the first approach using a random forest algorithm and the second approach using a convolutional neural network.

The basic principles of machine learning algorithms will now be briefly outlined.

A machine-learning algorithm is any self-training algorithm that processes input data in order to produce output data. Here, the input data may comprise a set of probability values of presence of an object in each frame, or the set of derived representative values for the radial lines. The output data comprises presence or absence of an object, and may further comprise a region of the data occupied by the object.

Suitable machine-learning algorithms for being employed in the present invention will be apparent to the skilled person. Examples of suitable machine-learning algorithms include decision tree algorithms (such as the random forest algorithm referred to above) and artificial neural networks. Other machine-learning algorithms such as logistic regression, support vector machines or Naïve Bayesian model are suitable alternatives.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

Methods of training a machine-learning algorithm are well known. Typically, such methods comprise obtaining a training dataset, comprising training input data entries and corresponding training output data entries. An initialized machine-learning algorithm is applied to each input data entry to generate predicted output data entries. An error between the predicted output data entries and corresponding training output data entries is used to modify the machine-learning algorithm. This process can repeated until the error converges, and the predicted output data entries are sufficiently similar (e.g. ±1%) to the training output data entries. This is commonly known as a supervised learning technique.

For example, where the machine-learning algorithm is formed from a neural network, (weightings of) the mathematical operation of each neuron may be modified until the error converges. Known methods of modifying a neural network include gradient descent, backpropagation algorithms and so on.

The training input data entries correspond to example a set of object presence probability values or a set of representative values for the complete set of radial lines. The training output data entries correspond to presence or non-presence of an object in the data and/or a region of the data occupied by an object (where present).

Following generation of the frame-wise sequence of object-presence probability values (such as the continuous probability value waveform shown in FIG. 15), the method 30 further comprises processing the values to determine based upon them at least one region of the ultrasound data (e.g. a consecutive sub-set of frames) occupied by an intravascular object.

Detecting the region occupied by the objects may make use of the fact that, particularly for man-made, artificial inserts, such as stents, grafts, guiding sheaths and guiding wires, the objects have a discrete and distinct size which causes the object to appear in multiple consecutive frames during pull-back of the IVUS device through the blood vessel lumen. This characteristic of continuous presence across a finite width region enables estimation of the region of occupation, particularly the longitudinal distal and proximal edges of the object along the longitudinal direction of pull-back.

Detection of a region of the data (e.g. set of consecutive frames) occupied by an intravascular object may comprise one of at least two approaches. A first approach may comprise searching for a consecutive region of frames having respective probability values all above a particular threshold, e.g. above 50% or above 60% or any threshold value that may be defined.

Another more complex approach comprises trialing a plurality of possible occupation regions within the data, evaluating a pre-defined cost function for each one (based on the derived set of probability values for the complete ultrasound data set), and then determining the most likely occupation region for any of one or more objects based on identifying the region having the minimum (or maximum) cost function result.

In either case, the approach may comprise identifying edges of an object and inferring the region of occupation based on the edge detection. Alternatively, the approach may comprise identifying the complete region of occupation without first identifying edges of the object.

The first approach is first outlined below.

According to the first approach, there may be first performed an initial processing step comprising temporally averaging or smoothing the probability values. By temporal is meant the dimension of incrementing frame number, i.e. the time domain corresponds to the frame number domain. Since, in operation, frames are captured at regular intervals, the frame index may effectively be understood as a temporal index. Averaging with respect to time (or across time) hence corresponds in this example to averaging with respect to incrementing frame number.

Hence according to one or more advantageous embodiments, a frame-wise filtering operation (temporal filtering operation) is performed which results in a sequence of locally temporally averaged probability values.

Figure 16:
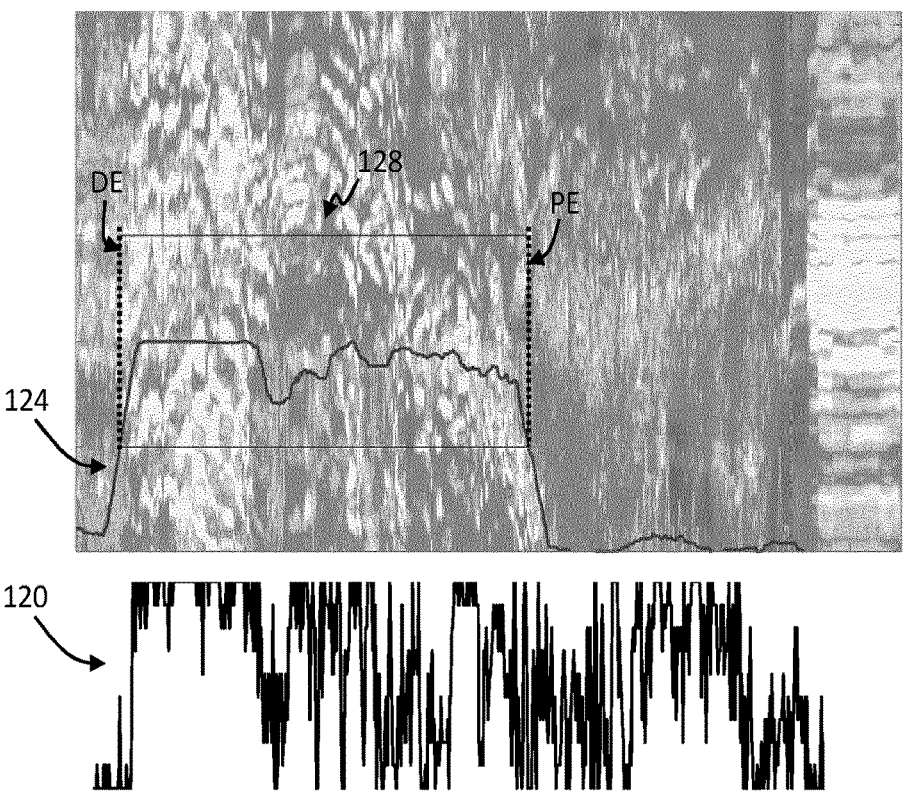
FIG. 16 shows an example time averaged probability curve derived from the probability values of FIG. 15.

An example sequence of filtered probability values, produced as an output of an example temporal filtering operation, is shown in FIG. 16. This example shows the filtered values 124 (in the form of a continuous probability curve) for the example set of raw probability values shown in FIG. 15 above. The filtered probability curve 124 is shown superposed atop the 2D map of representative values of FIG. 15 upon which it is based. For ease of reference, the raw set of probability values 120 is shown in FIG. 16 directly beneath the temporally-averaged probability curve 124.

In both FIG. 15 and FIG. 16, the respective probability curves 120, 124 are shown superposed upon the 2D map of representative values for each radial line (y-axis, azimuth angle) in each frame (x-axis; frame index), from which the probability values were derived. Both sequences of probability values (raw and temporally averaged) vary between a maximum of 100% (or 1) and 0% (0).

The temporal averaging or filtering averages out or filters over the frame index (x-axis) domain to smooth over the very rapid local variations in probability.

According to this first example approach, a region within the ultrasound data occupied by an artificial intravascular object may be detected based on applying a simple threshold to the set of averaged probability values. In particular, the approach comprises identifying a consecutive subset of frames for which the time-averaged probability values remain higher than a pre-defined threshold.

In advantageous examples, the pre-defined threshold may be 50%. In other examples, the pre-defined threshold may be greater than 50%, for example 60% or 70%. It may be lower than 50% in other examples. The threshold may be set depending upon the context, for instance depending upon how noisy is the obtained data, and the overall level of probabilities assigned to frames. For instance, where the data is noisy, and resulting probability values vary around a generally low region of probabilities, the threshold probability value may be set lower (and vice versa in the case of noisy data leading to a generally high set of probability values.

Identifying the consecutive set of frames having probability values above the pre-defined threshold may in examples comprise applying a rectangular low-pass filter (in the probability domain), and then applying the threshold to the output.

According to some examples, the procedure may comprise identifying the largest consecutive set of frames within the dataset having a probability value above the pre-defined threshold. This deals with situations where more than one region exists that meets the thresholding criteria. All regions may be selected as regions occupied by a respective object, or just the longest set of frames may be selected. There may be pre-stored prior information representative of expected typical width of a region occupied by the object in the data, and this information may be applied to select only one or more of any plural set of regions which are found as passing the probability threshold.

The procedure may in certain examples comprise a dynamic process of identifying the longest consecutive set of frames having the highest probability value. This may be an algorithm which applies different weightings to probability value versus length of set to identify the most likely region of occupation.

FIG. 16 shows the identified region 128 of consecutive frames within the data occupied by the object. The identified proximal edge ("PE") and distal edge ("DE") of the object are indicated by respective arrows.

The above approach has the advantage of being relatively simple, and therefore places low computational demand upon the processor carrying out the method.

A second approach for determining a region within the ultrasound data occupied by an intravascular object based on the probability values will now be outlined. This approach has been found to exhibit more robust and reliable performance in accurately identifying the region occupied by an object, for example detection of the edges of the object.

This second approach is based on testing a plurality of trial regions within the data, the testing comprising calculating for each trial region a difference between the set of probability values for the trial region and an equivalent set of probability values representative of exact occupation of the region by an object. The testing comprises in particular calculating a cost function, the cost function comprising, as a first term, the sum of said set of calculated difference values for the whole set of frames across the trial region. The cost function further comprises as a further one or more additive terms, a sum of the probability values for consecutive sets of frames on one or both sides of the trial region.

This approach will now be outlined in more detail.

This approach is based on the observation that the stent estimated presence tends to adopt a rectangular profile as a function of pull-back distance (or as a function of frame number). The concept comprises testing a plurality of hypotheses that an object, e.g. a stent, is present within the region (of frames) extending between frame d and frame p, where frame d and frame p contain respectively the distal and proximal object-edges (or vice versa). For every trial region (every trialed combination of edge position d and p) a cost function C(d,p) is calculated, associated with the given hypothesis that the object is present within that given region.

All possible regions of occupation may be trialed in some examples or, to save processing resource, and reduce processing time, just a subset of possible occupation regions of the object.

The cost function C(d,p) is calculated on the basis of the difference between the set of frame-by-frame (raw) probability values for presence of an object in each frame (calculated in the step outlined in examples above) and a test wave (e.g. a square wave) covering the trial region representative of 100% (or a defined figure) probability at every frame inside the trial region, and 0% probability outside the region. This test wave hence corresponds to certain (or a defined high) probability that the object occupies the trial region, and does not occupy any other region.

Figure 17:
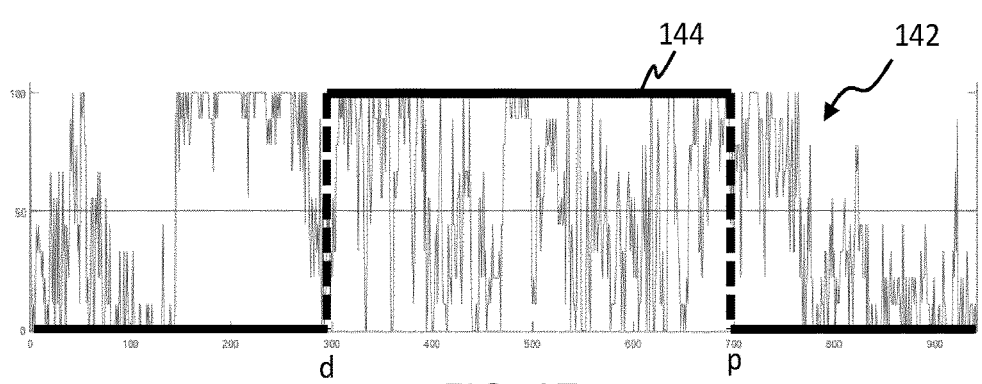
FIGS. 17 and 18 illustrate trialing of different trial regions of object occupation within a set of probability values based on application of a test square wave to different trial regions.

This is illustrated in FIG. 17 which shows the sequence of frame-wise probability values 142, with an example trial region test wave 144 superposed atop. The test wave in this case is a square wave.

The cost function is based on the difference between the trial region test curve 144 and the frame-wise probability values curve 142 in FIG. 17, and is given by:

$$C(d, p) = \sum_{i=0}^{d-1} |s(i) - 0| + \sum_{j=d}^{p} |s(j) - 1| + \sum_{k=p+1}^{L-1} |s(k) - 0|, \quad (3)$$

where s is the frame-wise object presence estimate (probability value) as a function of the frame index, and where L is the number of total number frames captured in the dataset (the number of frames captured during the full pullback through the blood vessel).

The procedure comprises identifying the values of d and p which minimize the cost, C, i.e. identifying the region (the consecutive set of frames) having the minimum value for the cost function.

The values of d and p that minimize C are taken as the estimated distal and proximal object edge locations.

Figure 18:
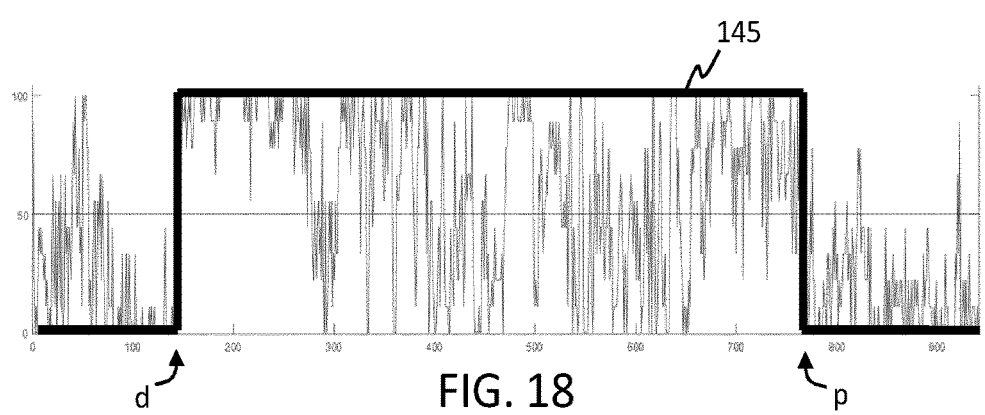

In the example set of probability values of FIG. 17, the values of d and p which result in minimum cost function are shown in FIG. 18. FIG. 18 shows the resulting minimum-cost trial region 145 of consecutive frames. This region 75 is hence provided by the algorithm as the derived region occupied by an intravascular object.

The direct calculation of C(d,p) involves the calculations of three summation terms for every combination of d and p. This is somewhat computationally inefficient.

A computationally faster approach may be considered. This approach is based on the initial calculation of two cumulative cost functions. The first function N(i) describes the cumulative cost of a "no-object" hypothesis between frame 0 and frame i, $$N(i) = \sum_{j=0}^{i} |s(j) - 0| = \sum_{j=0}^{i} s(j). \quad (4)$$

Figure 19:
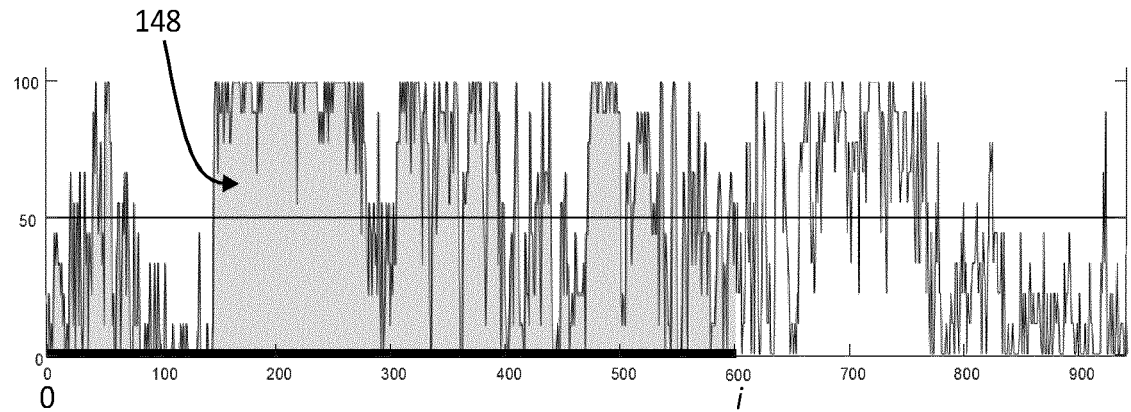
FIGS. 19-21 illustrate a variation of the approach of FIGS. 17 and 18, based on pre-calculation of two cost functions, the cost functions corresponding to different areas under a probability curve.

The value of N effectively describes the area 148 under the probability curve shown shaded in FIG. 19.

The second function S(i) describes the cumulative cost of a "object present" hypothesis between frame 0 and frame i, $$S(i) = \sum_{j=0}^{i} |s(j) - 1| = \sum_{j=0}^{i} 1 - s(j). \quad (5)$$

Figure 20:
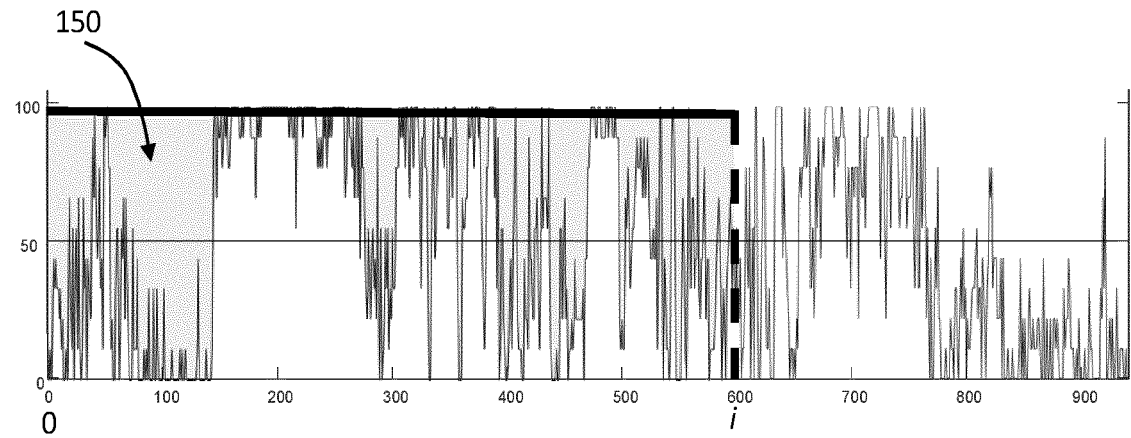

The value of S effectively describes the area 150 under the probability curve shown shaded in FIG. 20.

Using the pre-calculated cumulative cost function N(i) and S(i), each of the three summation terms of expression (3) above can now be more efficiently calculated in the following form:

$$C(d,p) = [N(d-1)] + [S(p) - S(d)] + [N(L-1) - N(p+1)]. \quad (6)$$

Figure 21:
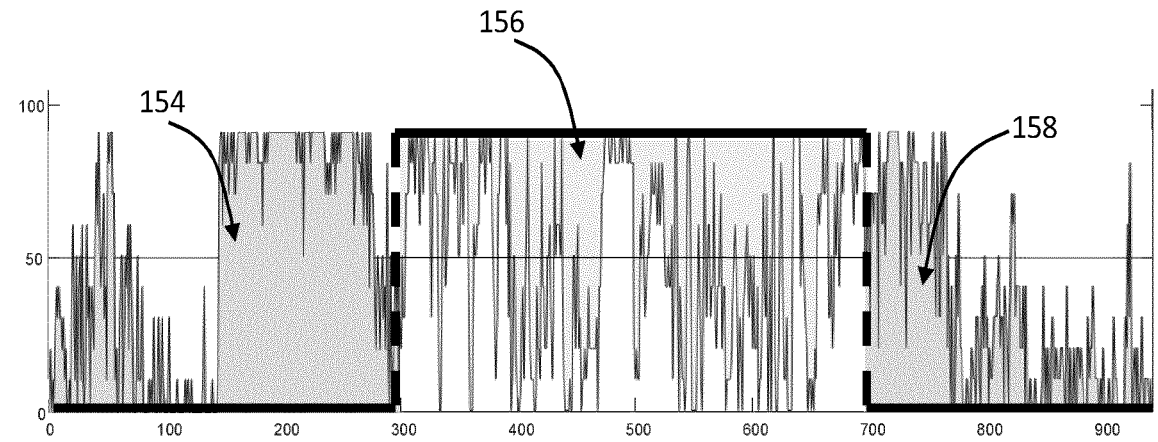

The associated areas for each of the three terms of equation (3) and (6) are depicted in FIG. 21, where shaded region 154 corresponds to the first term, region 156 to the second term, and region 158 to the third term.

The use of the pre-calculated cumulative cost functions, N(i) and S(i) has been demonstrated to increase the speed of the object region location estimation algorithm by a factor of around 300.

The increased speed can be understood from the fact that this approach pre-calculates the cumulative cost function for the two hypotheses (stent present, and no stent present) leading to two functions S(i) and N(i), as a function of the frame index. S(i) and N(i) may be understood as simply 1D arrays. Each cumulative cost function therefore takes only one parameter, rather than multiple parameters, leading to increases in speed.

In particular, in expression (6) it can be seen that each of the three summation terms (in expression (3)) is replaced by an evaluation using S(i) and N(i).

According to some examples, the method is configured to test all possible combinations of d and p, with the additional imposed constraint that p−d>M, where M is a pre-defined minimum number of frames that the object is expected to span. An increasing value of M reduces the number of trial regions that are tested, and hence increases algorithm speed, but at the cost of loss of detection capability for objects smaller than M frames.

According to some examples, the method may be applied for detection of location of a stent (e.g. stent edges) within data. However, detection of any other object is also possible, for example the region of consecutive frames occupied by a graft, a guiding sheath, or of a guide-wire. These represent just one limited set of examples.

According to one or more examples, an additional constraint may be imposed in the form of an assumption that the proximal edge of the object is always located at the last frame in the received dataset. Hence, here, p=L−1. This greatly reduces the complexity of the cost function calculation, and also reduces the number of cost functions that are required to be searched.

Use of this assumption may be particularly effective for detection of intravascular sheath edges for example. This is because, in practice, most IVUS pull-back scans end at the position of the guiding sheath. As the guiding sheath therefore tends to appear at the end of a pull-back, the last frame of a pull-back generally contains a guiding sheath. Therefore, it is a reasonable assumption in appropriate cases to fix the proximal edge p to be equal to the index of the last frame.

The inner diameters of guiding sheaths tend to be much smaller than the lumen of a healthy vessel. An automated search for the minimum lumen area is therefore likely to erroneously identify the frames containing a guiding sheath as diseased regions of the imaged vessel. The narrow guiding sheath is then mistaken for a stenosis. Thus, the ability to automatically identify the presence of a guiding sheath is valuable for avoiding this error.

According to one or more examples, the algorithm may be configured to test for the possibility an object is present in the received IVUS data which spans across the whole set of frames in a dataset. Hence, this allows the algorithm to successfully deal with situations in which the object is longer than the total length of the set of frames in the dataset, i.e. L<M.

The algorithm may in one or more examples be configured to allow for detection of more than one object within the set of frames, for instance two or more objects, spaced from one another.

Examples in accordance with a further aspect of the invention provide an ultrasound data processor for analyzing ultrasound data captured by an IVUS device. The processor is adapted to perform the following steps:

receive a plurality of frames of ultrasound data captured by the IVUS device, each frame comprising data for a plurality of radial scan lines, each radial scan line corresponding to an acoustic signal received along a different rotational angle (φ) with respect to a longitudinal axis (A-A') of the device;

process the ultrasound data for each radial scan line in each frame, to reduce the data for each line to a single representative data value for the line;

derive from the set of representative data values a set of probability values corresponding to probability of presence of an artificial intravascular object at least within each frame;

determine a region within the ultrasound data occupied by an intravascular object based on the probability values.

Implementation options and details for each of the above steps implemented by the processor may be understood and interpreted in accordance with the explanations and descriptions provided above for the method aspect of the present invention.

Any of the examples, options or embodiment features or details described above in respect of the method aspect of this invention may be applied or combined or incorporated mutatis mutandis into the present processor aspect of the invention.

The processor discussed above can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Examples in accordance with a further aspect of the present invention provide an ultrasound system.

The ultrasound system comprises an intravascular ultrasound, IVUS, device for capturing ultrasound data within a blood vessel lumen along a plurality of different radial scan lines; and an ultrasound data processor in accordance with any example or embodiment outlined above or described below, or in accordance with any claim of this application, operably coupled with the intravascular ultrasound device, and configured to receive ultrasound data captured by the IVUS device.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. An ultrasound system comprising:
a catheter with one or more imaging elements configured to capture a plurality of frames during a pullback of the catheter through a blood vessel, wherein a frame of the plurality of frames comprises:
  a frame number representative of a location along a length of the blood vessel and;
  a plurality of radial scan lines; and
an ultrasound data processor, operably coupled with the catheter, wherein the ultrasound data processor is configured to:
  process the plurality of radial scan lines for the plurality of frames into a set of maximum intensity pixel values such that a radial scan line corresponds to a maximum intensity pixel value;
  providing the set of maximum intensity pixel values to a convolutional neural network as an input, wherein the convolutional neural network is trained using a sample set of maximum intensity pixel values and training output data indicating a presence or non-presence of an object;
  generate, as an output of the convolutional neural network, a set of numerical probability values distinct from the set of maximum intensity pixel values, wherein, for the frame, a numerical probability value is representative of a likelihood that an artificial intravascular object is present at the location along the length of the blood vessel of the frame;
  determine, based on the set of numerical probability values, the frame number of a proximal edge of the artificial intravascular object and the frame number of a distal edge of the artificial intravascular object; and
  provide, to a display, an output comprising:
    a cross-sectional plane along the length of the blood vessel, wherein the cross-sectional plane comprises the plurality of frames; and
    a graphical representation based on the frame number of the proximal edge and the frame number of the distal edge, wherein the graphical representation corresponds to a region along the length of the blood vessel where the artificial intravascular object is present.

2. A method, comprising:
capturing, with one or more imaging elements of a catheter, a plurality of frames during a pullback of the catheter through a blood vessel, wherein a frame of the plurality of frames comprises:
  a frame number representative of a location along a length of the blood vessel; and
  a plurality of radial scan lines;
processing the plurality of radial scan lines for the plurality of frames into a set of maximum intensity pixel values such that a radial scan line corresponds to a maximum intensity pixel value;
providing the set of maximum intensity pixel values to a convolutional neural network, as an input, wherein the convolutional neural network is trained using a sample set of maximum intensity pixel values and training output data indicating a presence or non-presence of an object;
generating, as an output of the convolutional neural network, a set of numerical probability values distinct from the set of maximum intensity pixel values, wherein, for the frame, a numerical probability value is representative of a likelihood that an artificial intravascular object is present at the location along the length of the blood vessel of the frame;
determining, based on the set of numerical probability values, the frame number of a proximal edge of the artificial intravascular object and the frame number of a distal edge of the artificial intravascular object; and
providing, to a display, an output comprising:
  a cross-sectional plane along the length of the blood vessel, wherein the cross-sectional plane comprises the plurality of frames;
  and a graphical representation based on the frame number of the proximal edge and the frame number of the distal edge, wherein the graphical representation corresponds to a region along the length of the blood vessel where the artificial intravascular object is present.

3. The method of claim 2, wherein a radial scan line of the plurality of radial scan lines corresponds to an acoustic signal received along a different rotational angle with respect to a longitudinal axis of the catheter.

4. The method as claimed in claim 2, further comprising:
determining a consecutive subset of the plurality of frames occupied by the artificial intravascular object, or determining a consecutive subset of radial lines occupied by the artificial intravascular object.

5. The method as claimed in claim 2, further comprising:
determining a consecutive subset of frames for which the set of numerical probability values are each higher than a pre-defined threshold.

6. The method as claimed in claim 2, further comprising:
testing a plurality of trial regions within the plurality of frames, the testing comprising calculating for each trial region a difference between the set of numerical probability values for the trial region and an equivalent set of probability values representative of exact occupation of the region by the artificial intravascular object.

7. The method as claimed in claim 6,
wherein the testing comprises calculating a cost function, wherein the cost function comprises a sum of the calculated difference between the set of numerical probability values for the trial region and the equivalent set of probability values representative of the exact occupation of the region for each of the trial regions.

8. The method as claimed in claim 7, wherein the cost function comprises, as one or more further additive terms, a sum of the numerical probability values for a consecutive set of frames of the plurality of frames on at least one side of the trial region.

9. The method as claimed in claim 2, further comprising:
determining a set of index values representative of a location of each maximum intensity value along each radial scan line.

10. The method as claimed in claim 7, further comprising:
identifying, using the cost function, two minimum values of the cost function; and
outputting, to the display, a minimum cost trial region including the two minimum values.

11. The method as claimed in claim 10, wherein the two minimum values represent the distal edge and the proximal edge of the artificial intravascular object.

12. The method as claimed in claim 2,
further comprising generating a plot or map of the set of maximum intensity pixel values,
wherein the plot or map represents the values plotted against frame number and/or radial line number.

13. The method as claimed in claim 2,
wherein generating the set of numerical probability values comprises detecting, within the set of maximum intensity pixel values, one or more characteristic patterns characteristic of presence of the artificial intravascular object.

14. The method as claimed in claim 2, wherein each frame corresponds to a different longitudinal location along the blood vessel.

* * * * *